United States Patent [19]
Johnson

[11] Patent Number: 5,765,224
[45] Date of Patent: Jun. 16, 1998

[54] BODY SUPPORT GARMENT

[76] Inventor: Christina Erteszek Johnson, 21914 Goldstone Rd., Topanga, Calif. 90290

[21] Appl. No.: 746,861

[22] Filed: Nov. 18, 1996

Related U.S. Application Data

[63] Continuation-in-part of Ser. No. 685,962, Jul. 22, 1996, which is a continuation of Ser. No. 236,085, May 2, 1994, Pat. No. 5,537,690.

[51] Int. Cl.⁶ .................... A61F 5/02; A41C 1/00
[52] U.S. Cl. .................... 2/44; 2/45; 602/19
[58] Field of Search ............ 2/44, 45, 92; 602/19; 450/107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146

[56] References Cited

U.S. PATENT DOCUMENTS

| | | |
|---|---|---|
| 198,348 | 12/1877 | Chapman . |
| 604,296 | 5/1898 | Caroli . |
| 1,170,282 | 2/1916 | Kops . |
| 1,203,020 | 10/1916 | Leopold et al. . |
| 1,603,868 | 10/1926 | Rosenman . |
| 1,636,459 | 7/1927 | Chappel . |
| 1,753,739 | 4/1930 | Burns . |
| 1,755,641 | 4/1930 | Foulke . |
| 2,048,531 | 7/1936 | Yerkes . |
| 2,088,423 | 7/1937 | Kispert . |
| 2,115,398 | 4/1938 | Rosenthal . |
| 2,341,882 | 2/1944 | Scriggins . |
| 2,596,765 | 5/1952 | Dubner . |
| 2,603,787 | 7/1952 | Leventhal . |
| 2,733,444 | 2/1956 | Goldstein . |
| 3,099,266 | 7/1963 | Spitzer . |
| 3,115,880 | 12/1963 | Blair . |
| 3,282,264 | 11/1966 | Connelly . |
| 3,441,027 | 4/1969 | Lehman . |
| 3,603,316 | 9/1971 | Lehman . |
| 3,812,862 | 5/1974 | Bernstein . |
| 3,945,041 | 3/1976 | Rhee . |
| 4,398,538 | 8/1983 | Johnson . |
| 4,681,113 | 7/1987 | Coplans . |
| 4,745,911 | 5/1988 | Bender ........................... 602/19 |
| 5,111,806 | 5/1992 | Travis . |
| 5,205,815 | 4/1993 | Saunders . |
| 5,221,227 | 6/1993 | Michels . |
| 5,399,151 | 3/1995 | Smith ............................. 2/44 |
| 5,537,690 | 7/1996 | Johnson . |
| 5,560,046 | 10/1996 | Iwamasa et al. ............ 602/19 |

*Primary Examiner*—Jeanette E. Chapman
*Attorney, Agent, or Firm*—William W. Haefliger

[57] ABSTRACT

A torso-shape controlling, lower back supporting garment that comprises a garment having control fabric panel portions adapted to extend in waist shape controlling relation to torso front, back and sides; the control fabric panel portions including zones positioned to be generally rigid at the torso front and back and to yieldably resiliently stretch generally horizontally at the torso sides, whereby support is provided at the lower back, and an hourglass torso shape at the waist is produced; and auxiliary structure extending in proximity to certain of said first control fabric panel portions to enhance the waist shape controlling functioning.

21 Claims, 11 Drawing Sheets

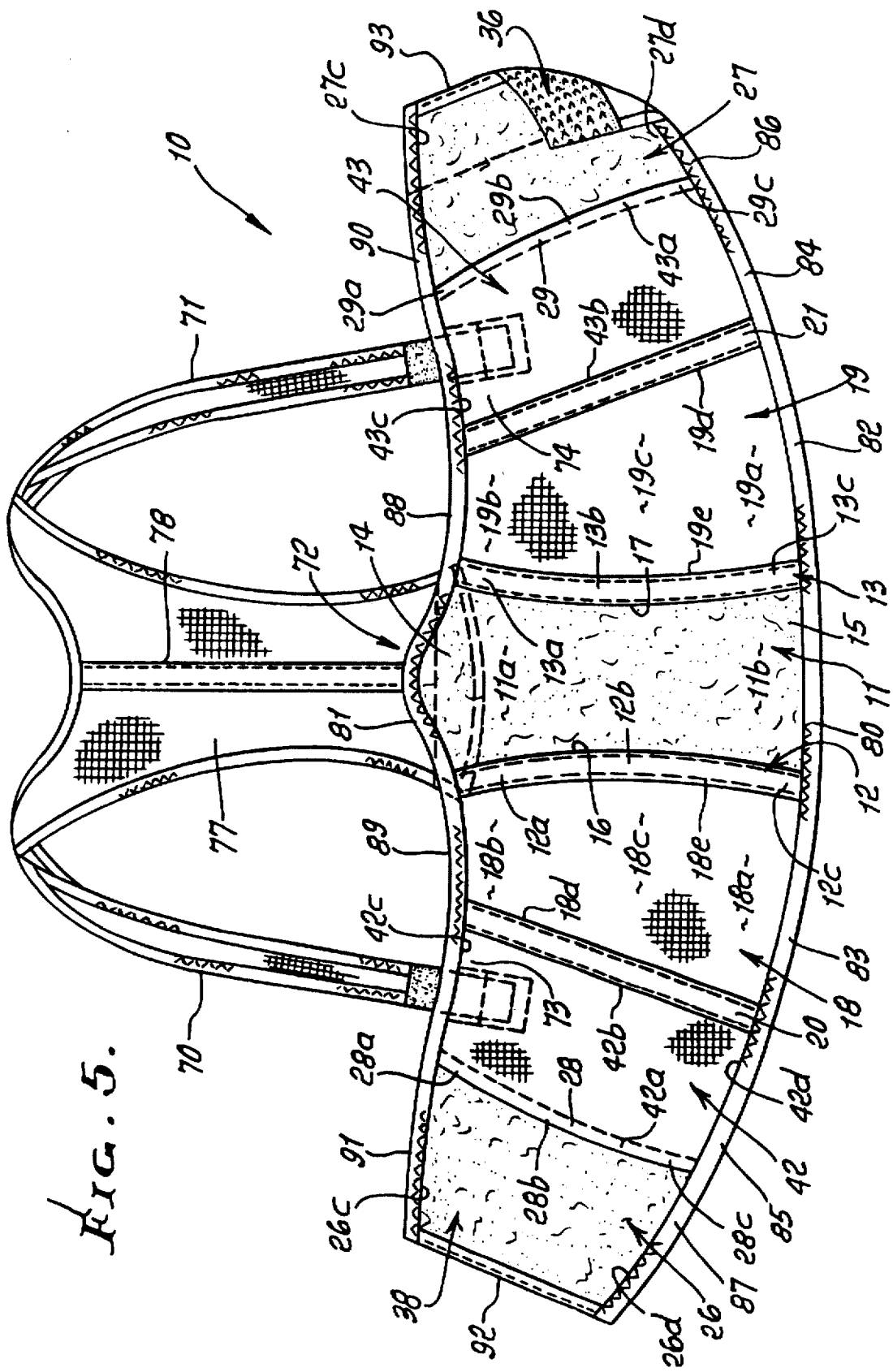

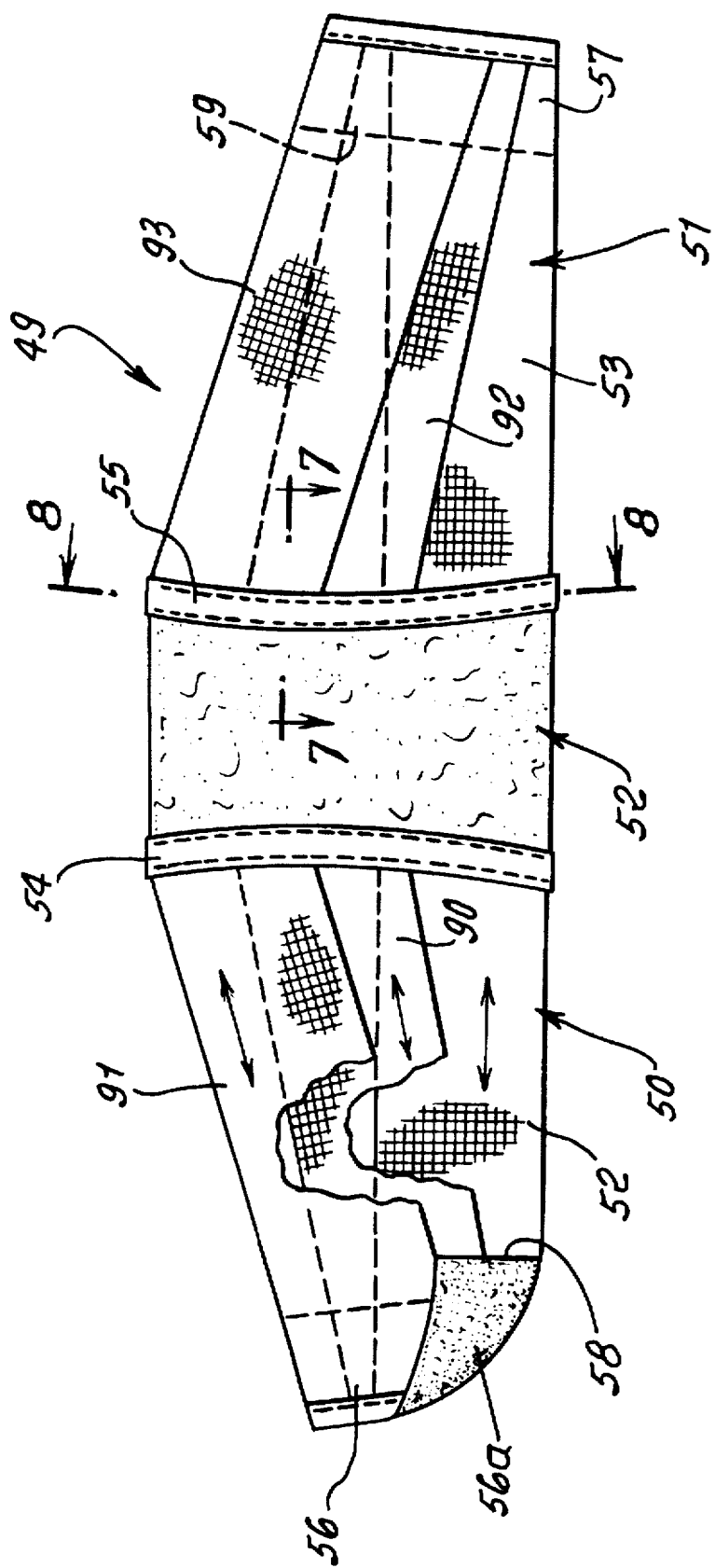

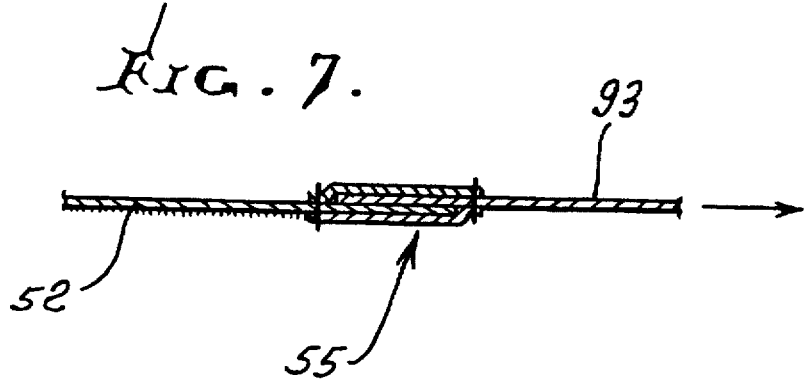
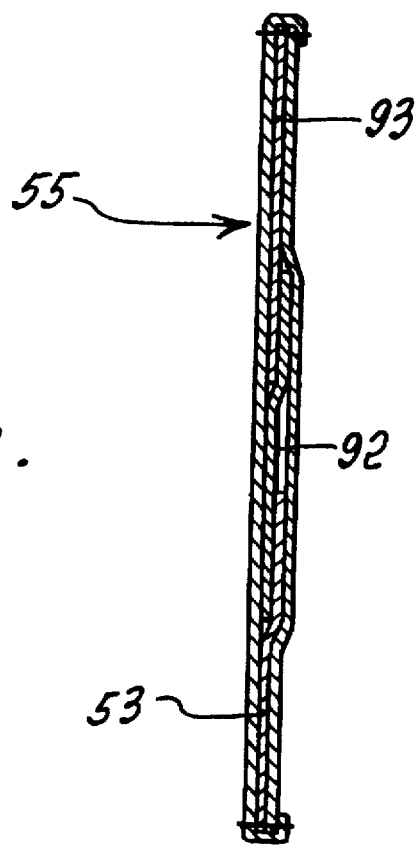

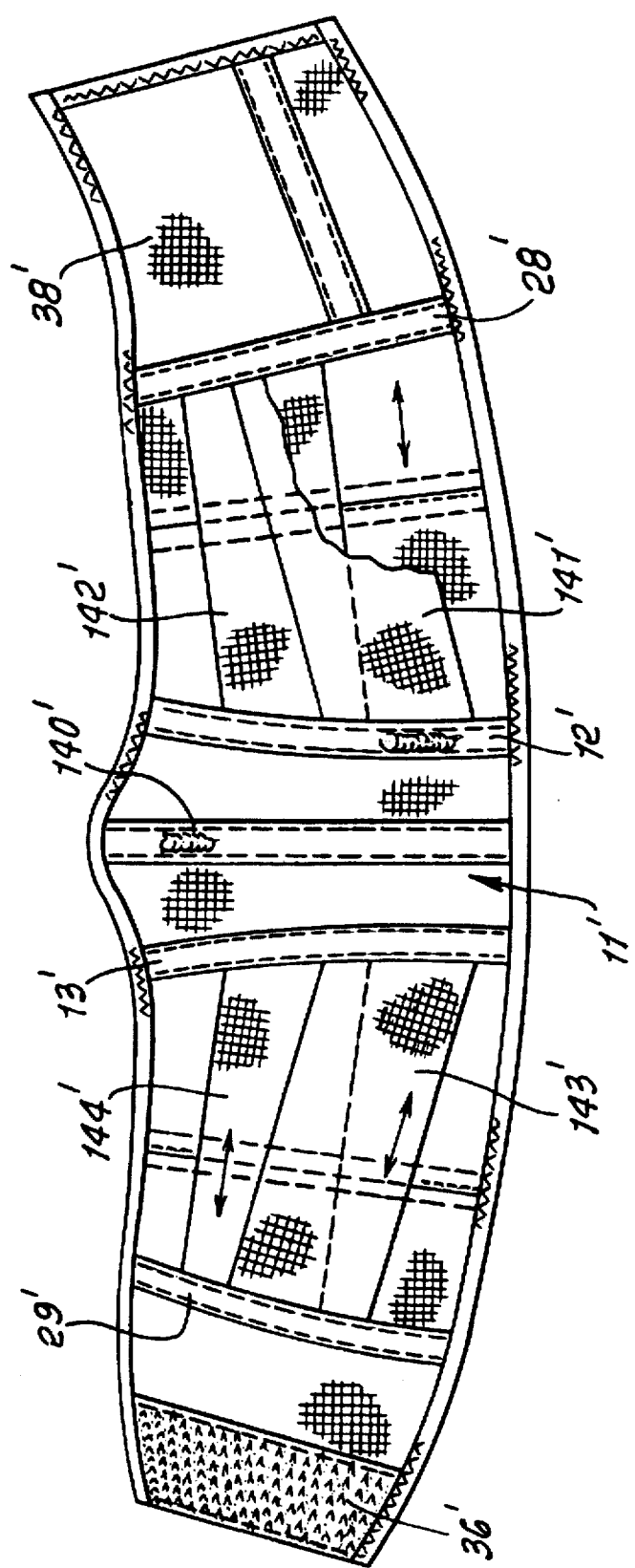

5,765,224

1

BODY SUPPORT GARMENT

This application is a continuation-in-part of prior U.S. application Ser. No. 08/685,962 filed Jul. 22, 1996, which is a continuation of prior U.S. application Ser. No. 08/236,085 filed May 2, 1994, now U.S. Pat. No. 5,537,690.

BACKGROUND OF THE INVENTION

This invention relates generally to human torso control, as at the waist region, and more particularly, to an improved garment that provides support and protection to the lumbar region of the back, as well as maintaining an "hourglass" or reduced shape of the human torso at the waist.

Extensive studies have shown that back supports aid significantly in helping to reduce back injuries, especially among those people who lift heavy loads, repeatedly. More than one million workers suffer back injuries each year, accounting for one out of every five workplace injuries and illnesses. Moreover, back injuries account for one-fourth of all workers compensation claims, costing businesses billions of dollars each year.

Back supports have become standard issue for a wide variety of workers over the past several years, despite there being little scientific inquiry into whether the devices help prevent injuries. The benefits of using the back supports were seen in both men and women workers, in young and older workers, and among workers engaged in both low and high levels of lifting, according to researchers. The greatest benefit was seen among the groups of workers at highest risk of back injury—men who were 25 and young or over age 55, had worked one to two years, and had jobs that required the highest intensity of lifting.

It will, therefore, be seen that there is great need for improvements in back supports, especially for use by women who need extra support at the abdominal region, as well as at the reduced waist region, and the lumbar region. Previously, back supports were designed and constructed primarily for use by men, and did not take into account the special shape and contour requirements of women's figures, i.e., at the narrowed waist region, and also associated with the lumbar region.

Accordingly, there is need for improvements in back supports, specifically designed for use by women, and which provide controlled, comfortable compression resulting in improvements in posture control as during lifting, controlled pressure on the lower abdomen, and local controlled pressure at the reduced waist region acting to achieve pressure through the body, for control of the lumbar region.

There is also need for an effective, comfortable support garment that conforms to the contours of a human, and specifically a woman; achieves or enhances an "hourglass" or reduced look or shape of the female torso, and that simultaneously creates control or compression at the front ("tummy" region) and also at the back (lower lumbar region). Versatile adjustment of such a garment is also needed, to comfortably conform readily to a wide range of figures.

SUMMARY OF THE INVENTION

It is, therefore, a major object of the invention to provide an improved garment meeting the above multiple needs. Basically, the torso-shape controlling, lower back supporting garment comprises, in combination:

a) the garment having control fabric panel portions adapted to extend in waist shape controlling relation to torso front, back and sides,

2 b) the control fabric panel portions including zones positioned to be generally controllable at the torso front and back, and to yieldably resiliently stretch generally horizontally at the torso sides, whereby an hourglass or reduced torso shape at the waist is produced, and whereby support is provided at the lower back. The generally rigid panel zones may be vertically stretchable, yieldably resiliently, but not horizontally, stretchable, and c) means to enhance the shape-controlling functions of the shape-controlling fabric panel portions.

As will be seen, the achieved hourglass shape prevents "ride-up" of the garment.

It is another aspect of the invention to provide shape-control enhancement, as by means of auxiliary control fabric panel means includes multiple overlapping sub-panels which are yieldably resiliently stretchable in directions extending about the first control fabric panel portions.

A further object is to provide overlapping means to include multiple elements which are yieldably resiliently stretchable in directions extending about the first control fabric panel portions. As will be seen, such elements may overlap vertically to enhance the control function.

A yet further object is to provide two sets of elements, and an intermediate element, which is substantially non-stretchable, in said directions.

An added object is to provide auxiliary means in the form of auxiliary control fabric panel means wrapped about the first control fabric panel portions, and having end extents which are interconnected to cause the auxiliary panel means to exert inward compression against the first control fabric panel means. In this configuration, the sub-panels may overlap vertically giving enhanced tensioning, girdlewise; and there may be two sets of such stretchable sub-panels.

An additional object is to provide such multiple elements at the inner sides of certain control panels, and in the form of elastic members that interconnect stiffener regions of the garment. Such stiffener regions typically extend upwardly adjacent resiliently non-stretchable portions of the garment.

These and other objects and advantages of the invention, as well as the details of an illustrative embodiment, will be more fully understood from the following specification and drawings, in which:

DRAWING DESCRIPTION

FIG. 5 is an enlarged elevation showing the inner side of the inner garment structure in FIG. 1, in unwrapped condition;

FIG. 6 is an enlarged elevation showing the inner side of the outer garment structure of FIG. 1, in unwrapped condition;

FIG. 7 is an enlarged section taken on lines 7—7 of FIG. 6;

FIG. 8 is an enlarged section taken on lines 8—8 of FIG. 6;

FIG. 14 is an enlarged elevation showing the outer side of the FIG. 13 modified garment structure, in unwrapped condition.

DETAILED DESCRIPTION

Figure 1:
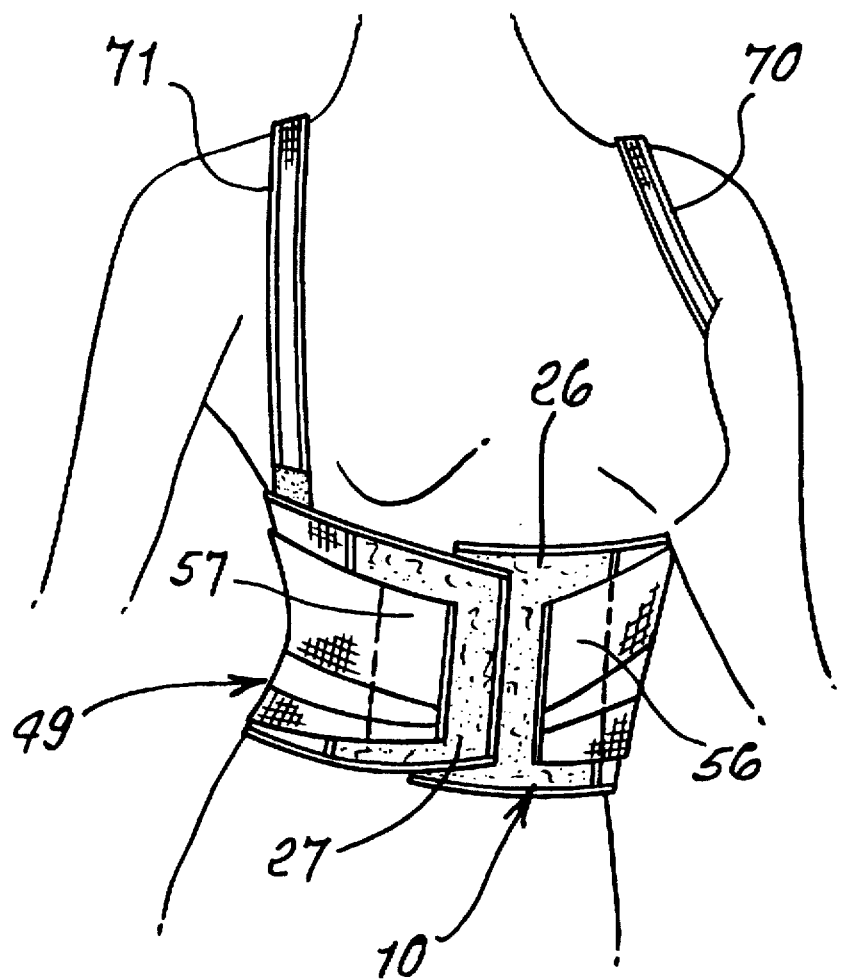
FIG. 1 is a front view of inner and outer garment structures incorporating the invention and fitted on a user.

Basically, the preferred garment shown in the drawings is characterized as having control fabric portions adapted to extend in waist-shape controlling, lower back supporting relation. The garment is also characterized as having control fabric panel portions adapted to extend in waist shape controlling relation to torso front, back and sides, whereby an hourglass torso shape at the waist is produced. Further, the garment is characterized in that the control fabric panel portions include zones positioned to be generally rigid at the torso front and back, and to yieldably resiliently stretch generally horizontally at the torso sides, whereby support is provided at the lower back, and the hourglass shape is produced.

More specifically, in the FIG. 5 illustrated example, the garment 10 has fabric portions as follows:

i) control fabric panel 11 at the garment rear, to face the lower back of the user's torso, at the waist, panel 11 having planar hourglass shape (i.e., downwardly convergent and then divergent at regions 11a and 11b between stay zones 12 and 13, arcuate at 12a, b and c and 13a, b and c).

Panel 11 is generally rigid, but may be resiliently yieldably stretchable, to limited vertical extent, but not horizontally stretchable between stays 12 and 13, to "hold in" the user's torso at the back, during forward bending at the waist area, thereby providing lower back support concentrated at the spine area, in part due to the hourglass shape of panel 11.

Panel 11 is vertically elongated between upper and lower edges 14 and 15, and between oppositely curved side edges 16 and 17. Panel 11 may consist of polyester strands woven to provide panel rigidity (substantial nonflexibility), but may have limited elasticity to allow vertical stretchability, as referred to.

ii) control fabric panels 18 and 19 at the garment sides, to face the wearer's torso at the waist opposite sides.

Panel 18 extends between horizontally spaced stay zones 20 and 12; and like panel 19 extends between horizontally spaced stay zones 21 and 13. Each of panels 18 and 19 is typically wider at its lower extents 18a and 19a, than at its top and medial zones 18b and 18c, and 19b and 19c.

Figure 2:
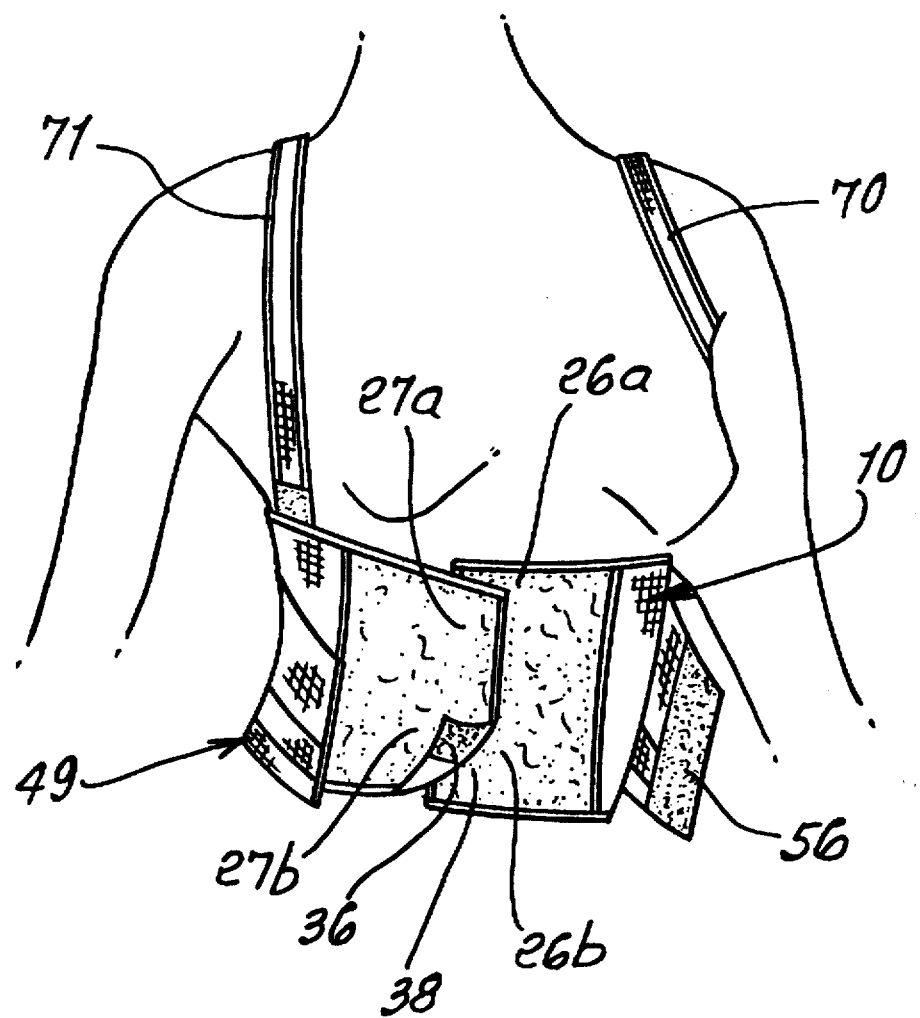
FIG. 2 is a view like FIG. 1 showing partial removal of the outer garment structure.
Figure 3:
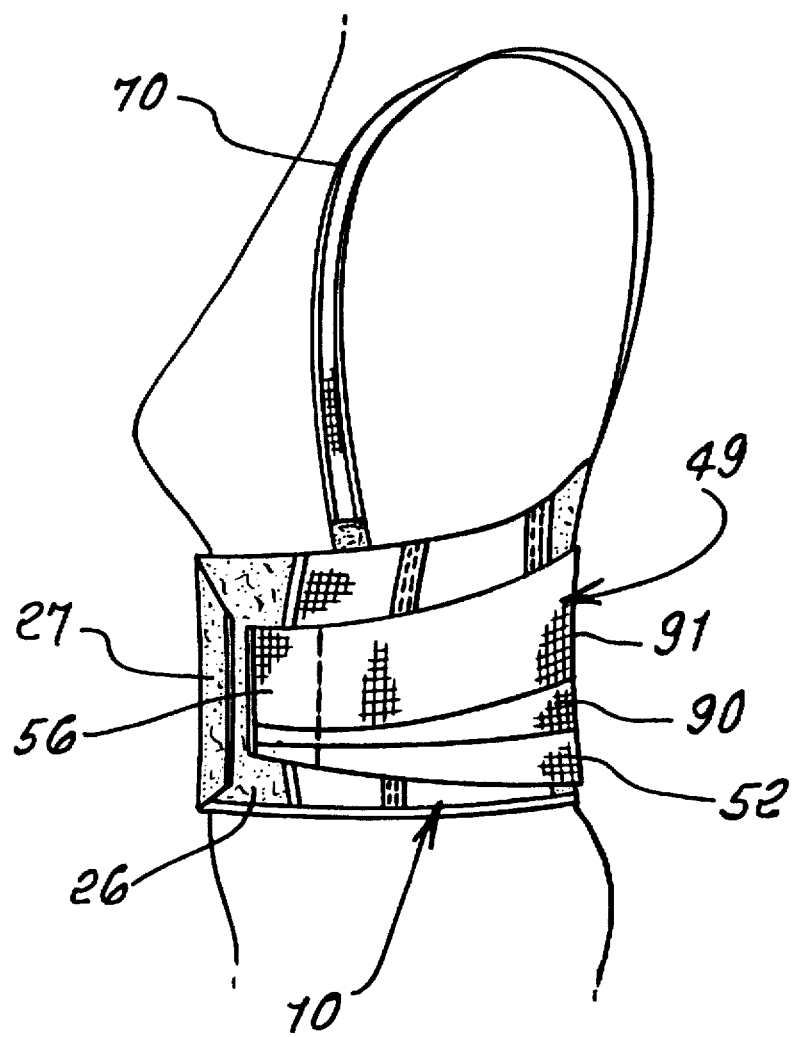
FIG. 3 is a left side elevational view of the garment structure, as seen in FIG. 1.
Figure 4:
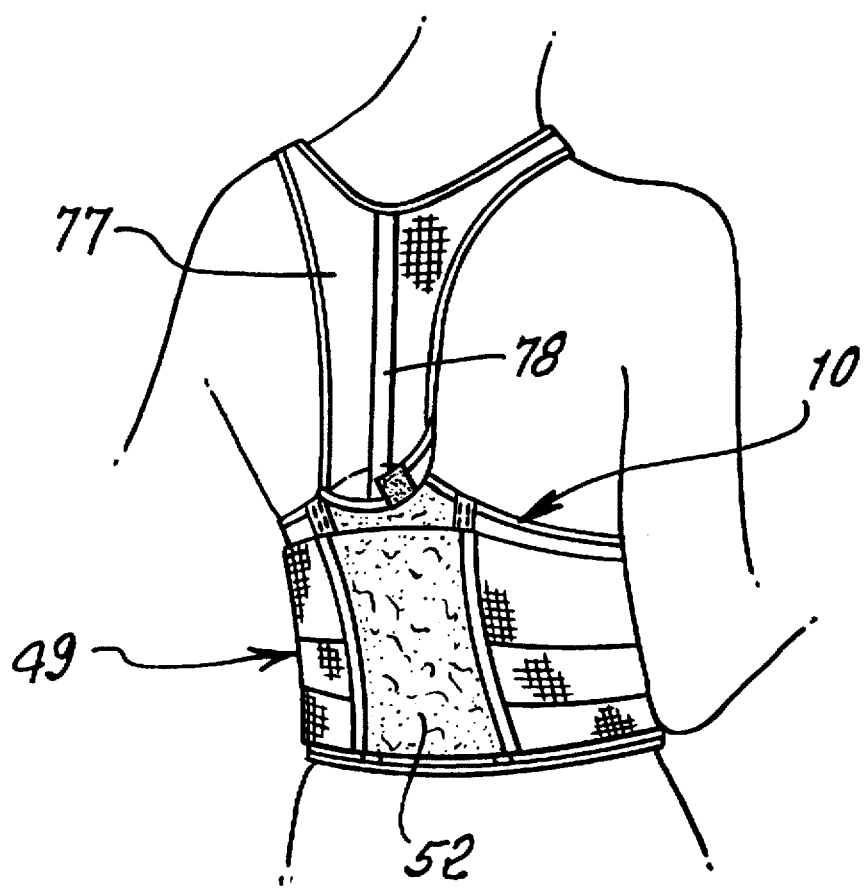
FIG. 4 is a rear side elevational view of the garment structure, as seen in FIG. 1.

Side edges of the panels 18 and 19, adjacent the stay zones, are designated at 18d and 18e, and 19d and 19e. See FIG. 5. Each of the panels 18 and 19 may consist of the known NYLON fabric "POWER NET" and is resiliently yieldably stretchable, both horizontally and vertically (but preferably more stretchable horizontally than vertically). Two layers of such fabric can be used.

iii) interconnectible control fabric panels 26 and 27 at the garment front, to face and control the wearer's torso at the waist front, i.e., "tummy zone", when interconnected, as will be described. The panels 26 and 27, when connected, have overall planar hourglass shape, i.e., downwardly convergent and then divergent, as seen in FIG. 2, at combined upper regions 26a and 27a, and at combined lower regions 26b and 27b, between curved zones 28 and 29, arcuate at 28a, b and c; and at 29a, b and c. Zones 28 and 29 are connection zones between panel 26 and a panel 42 (described below); and between panel 27 and a panel 43 (described below).

The panels 26 and 27 are generally rigid and are not vertically resiliently yieldable or stretchable, between upper and lower edges 26c and 26d, and between upper and lower edges 27c and 27d and are not horizontally stretchable, whereby the front of the wearer's waist is not allowed by panels 26 and 27 themselves to expand outwardly, aiding the torso hourglass shape control to be achieved.

The panels 26 and 27 interconnection may be advantageously achieved, as by VELCRO-type hooks at 36, on the underside of panel 27; and VELCRO-type loops at 38, on the front side of panel 26, the hooks engaging the respective loops when the panels are pressed together in overlapping relation, as seen in FIGS. 1 and 2. The area of loops 38 is quite large to provide for tightening or loosening of the garment, if desired, although the horizontal stretchability of panels, as referred to, allows for size adjustment. Multiple sizes of the garment are contemplated to enable use by persons of all waist sizes.

iv) control fabric panels 42 and 43, as referred to at transitions between panels 26 and 18, and between panels 27 and 19, are provided to allow tightening and loosening adjustment of the garment about the wearer's waist.

Panel 42 is attached at horizontally spaced, upright edges 42a and 42b to panels 26 and 18. Like panel 43 is attached at its horizontally spaced upright edges 43a and 43b to panels 27 and 19, as shown.

Panels 42 and 43 are each horizontally and vertically resiliently yieldably stretchable to accommodate to the torso at the waist, to allow torso bending; and also to accommodate tightening and loosening adjustment about the waist. Upper and lower edges of panels 42 and 43 are indicated at 42c and 42d, and at 43c and 43d.

All panels 18, 42, 14, and 43 are flexible, i.e., bendable, to conform to the wearer's waist. Also, panels 18, 42, 14, and 43 may each consist of two layers of fabric.

Accordingly, control fabric panel portions are provided to include zones positioned to be generally non-stretchable at the torso front and back, and to yieldably resiliently stretch generally horizontally at the torso sides, whereby support is provided at the lower back, and an hourglass torso shape at the waist is enhanced.

As referred to, tightening and loosening of the garment is provided for, while maintaining back support, as well as tummy control, at the torso front, as referred to, thereby creating better posture.

AUXILIARY CONTROL

Also provided, for use as desired with the form of the invention seen in FIGS. 1–12, is auxiliary means extending in proximity to certain of the first control fabric panel portions to enhance the waist-shape controlling functioning. This enables optimal use of the auxiliary control means, in conjunction with the simplified wrap 10. As will be seen, such auxiliary means typically includes multiple elements which are yieldably resiliently stretchable in directions extending about the first control fabric panel portions. Such elements typically may overlap vertically; and may be provided in two sets, with an intermediate element, which is substantially non-stretchable located between those sets of elements in a wrap form of the auxiliary means adapted to be independently overlapped about the first control fabric panels previously described.

Also, for simplicity, ease of application and removal, and enhanced effectiveness, the opposite ends of the auxiliary means may removably attach to different portions of the interconnected end panels 26 and 27, as described, as by hook and pile (VELCRO) attachment, allowing vertical adjustability of the auxiliary control means relative to the garment 10.

In the example shown in FIG. 6, the auxiliary wrap structure 49 (belt-band) includes control flaps 50 and 51, provided to extend horizontally and oppositely from an intermediate non-stretchable panel 52, similar to panel 11 in FIG. 5. The flaps 50 and 51 includes panels 52 and 53 which are horizontally yieldably stretchable in the same manner as panels 18 and 19. Panels 52 and 53 are connected via upright stay zones 54 and 55 (containing rigidizing strap) to panel 52. Non-stretchable connection panels 56 and 57 carrying VELCRO connections are joined to stretchable panels 52 and 53, as at zones 58 and 59. Panel 56 is turned back at 56a to show such VELCRO. Panels 56 and 57 adjustably attach to the surface of panel 26, as seen in FIG. 1.

Multiple endwise resiliently yieldable strap elements or elastic straps are provided as shown, to substantially increase the force required to endwise stretch the wrap structure 49. See multiple (dual) straps 90 and 91, loosely overlying panel 52 and endwise joined to 54 and 56, and multiple (dual) straps 92 and 93 loosely overlying panel 53 and endwise joined to 55 and 57. Note vertical overlap of straps 90 and 91, along their lengths, and vertical overlap of straps 92 and 93, along their lengths.

FIGS. 1 and 2 show the manner in which panels 56 and 57 respectively attach to panels 26 and 27. The areas of VELCRO are such as to allow a considerable degree of vertical up and down adjustment shifting of 56 on 26, and of 57 on 27. This in turn allows up and down shifting of the over-wrap 49 to accommodate to the torso of the wearer, and to the "under" garment 10 initially wrapped about the torso, at the waist. Accordingly, the enhanced securing, clamping force of wrap 49, over wrap garment 10, may be adjusted for comfort and for best positioned and enhanced support for the torso. Back panels 52 and 11 may also have mutual hook and pile (VELCRO) attachment, and with wide range up and down, and left and right relative position adjustability, for anchoring adjustment of the two wraps 10 and 49, at the back, proximate the lumbar region.

Fabric panels 18 and 42 accommodate themselves to this tightening or loosening, by flexing; and stays at zones 12 and 20, maintain the shapes of the flexing panels 18 and 42, adjacent thereto, as well as urging them toward or against the hourglass-shaped torso, under the influence of the auxiliary wrap 49.

Likewise, fabric panels 19 and 43 accommodate themselves to this tightening or loosening, as by flexing. Although tensioned medially thereof, stays at zones 13 and 29 maintain the shapes of the flexing panels 19 and 43 adjacent thereto, as well as urging them toward or adjacent the hourglass-shaped torso, under the influence of the wrap 49.

A compact, flat composite of flaps and fabric panels, and stays, is achieved, to protect the lower back (lower lumbar) region, and yet maintain an hourglass shape, flat tummy, to enable rapid adjustability at both sides of the torso or waist, and to enhance alignment for proper posture.

Figure 9:
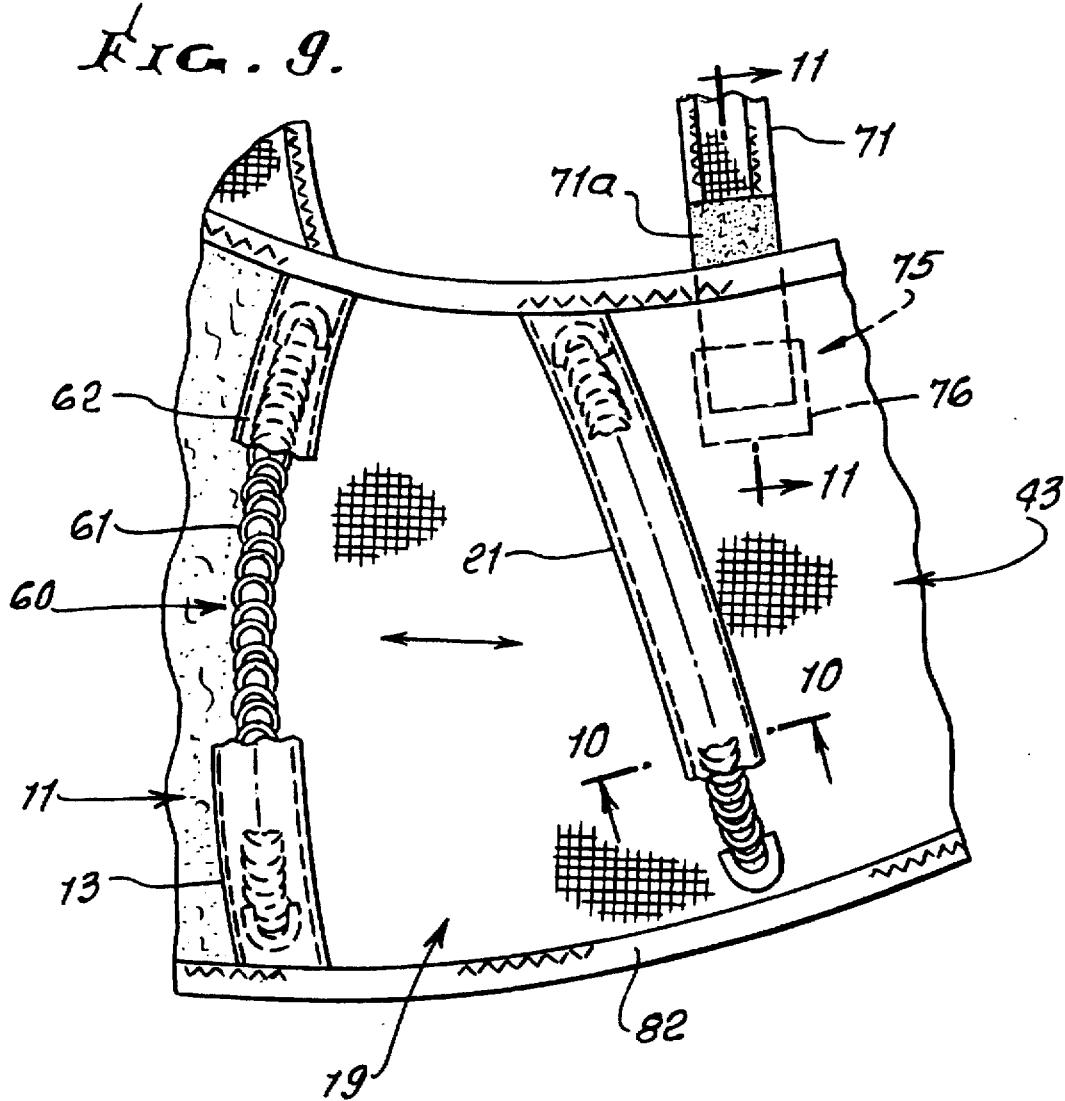
FIG. 9 is a further enlarged fragmentary view showing a portion of the inner garment, as seen in FIG. 5, and partially broken away to show detailed construction.
Figure 10:
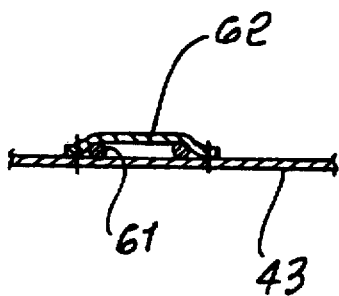
FIG. 10 is a section taken on lines 10—10 of FIG. 9.

Stays 60, at stay regions 12, 20, 13, and 21, may take the form as shown in FIG. 9. They are elongated, metallic and flexible. They may take the form of small steel loops 61 that spiral loop-interconnect together, as is known. They are confined in the stay zones, as by jacketing 62, which also serves to interconnect ends of adjacent panels. The stays also allow for rotational torso movement.

Figure 11:
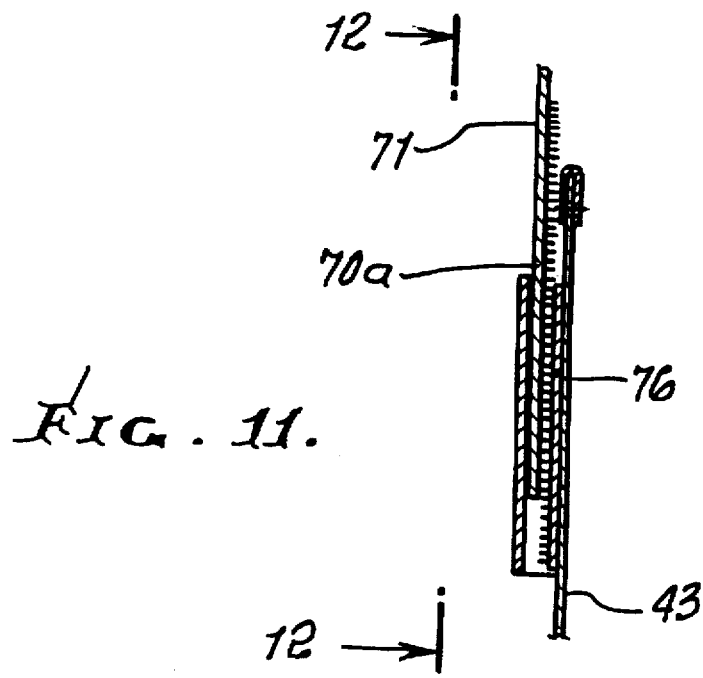
FIG. 11 is a section taken on lines 11—11 of FIG. 9.
Figure 12:
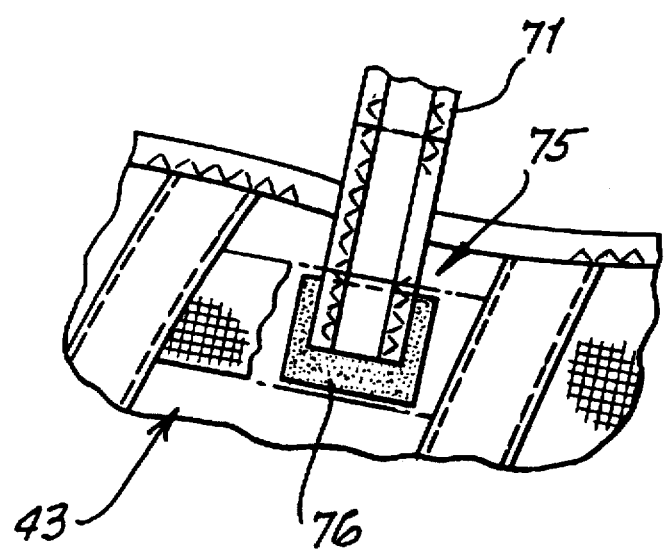
FIG. 12 is an elevation taken on lines 12—12 of FIG. 11.

Shoulder straps 70 and 71 may be provided, as shown, to connect at 72 to upper extent of back panel 11, and to connect to upper extents 73 and 74 of panels 42 and 43. A typical connection at 75 is shown in FIGS. 9 and 11 as vertically adjustable, as via VELCRO pad 76 on upper extent 73 of panel 42, and VELCRO end 70a of strap 71. Vertical adjustability (lengthening or shortening) of the shoulder straps is thereby provided, by VELCRO attachment adjustment, to accommodate to the size of the wearer. Note also medial panel 77 between back extents of straps 70 and 71, and a vertical back panel stiffener 78.

Figure 13:
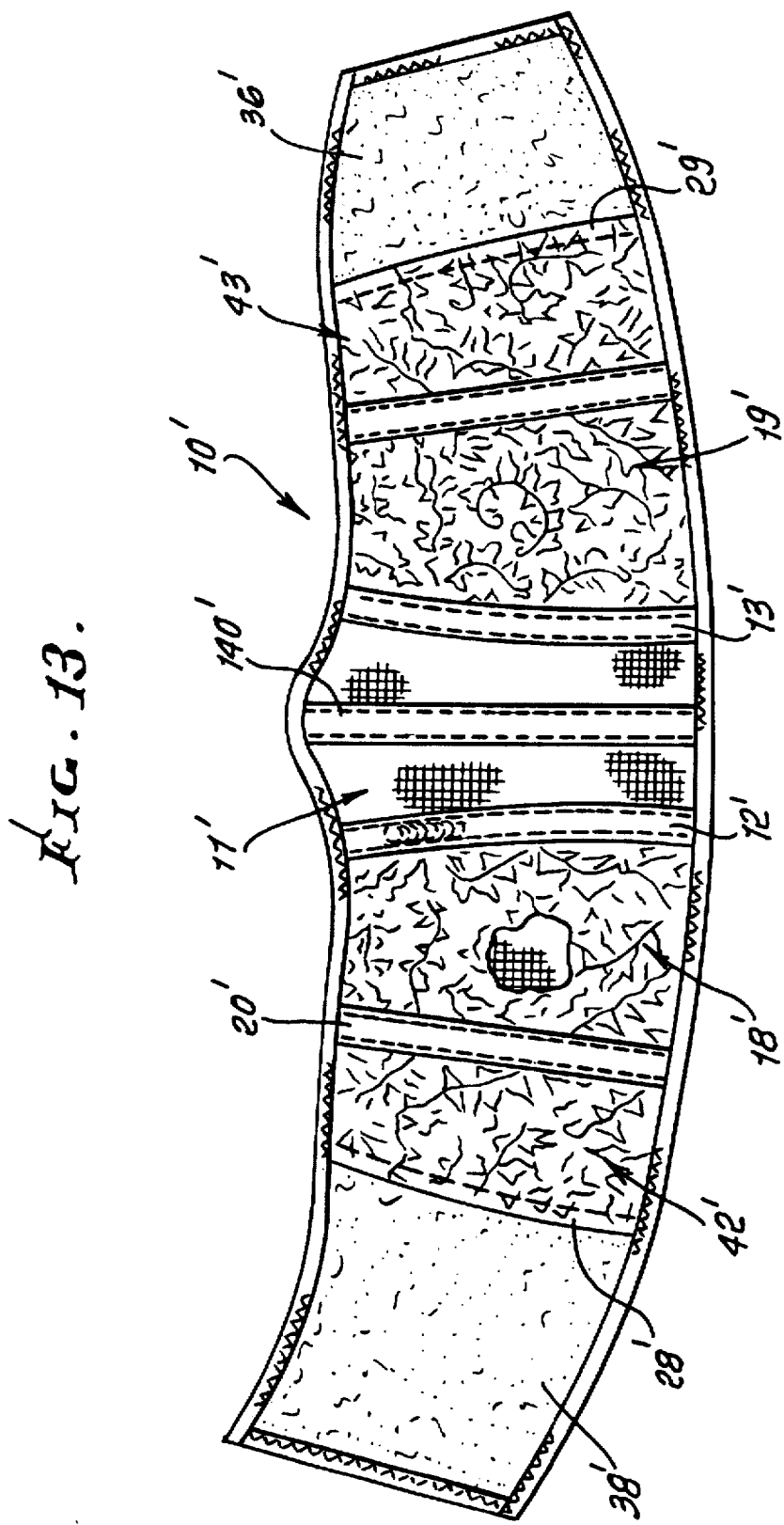
FIG. 13 is an enlarged elevation showing the inner side of a modified inner garment structure, in unwrapped condition.

FIGS. 13 and 14 show a form of the garment 10' that lacks shoulder straps, but is otherwise substantially the same as garment 10. Corresponding elements bear the same identifying and primed numerals. Note also in FIG. 14 that the panels 18', 19', 42', and 43' have lace surfacing, so that 10' may be worn as an intimate or more stylized garment. Elastic bands may be constructed with this garment.

Note also addition of a medial, vertical stiffener 140' in panel 11'; and horizontal, elastic straps 141' and 142' extend between end connections to 12' and 28'; and horizontal, elastic straps 143' and 144' extend between end connections to 13' and 29'. Such straps enhance tightness control.

Yieldably resiliently stretchable seam binding is also provided along edges of the FIG. 5 garment and panels, as indicated at 80–93.

It will be noted that by having different parts, 10 and 49, the garment enhances support and control flexibility; and either part can be independently worn, as an inner or outer garment. These advantages are enabled by the construction of the parts, aiding removability and dependability. By combining these as described herein, extra support and compression are provided where needed, especially as respects the female figure and wide range relative position adjustability is also provided.

I claim:

1. In a torso-shape controlling, lower back supporting garment the combination comprising:

a) said garment having control fabric panel portions adapted to extend in waist shape controlling relation to torso front, back and sides, b) said control fabric panel portions including zones positioned to be generally non-stretchable at the torso front and back, and to yieldably resiliently stretch generally horizontally at the torso sides, whereby support is provided at the lower back, and an hourglass torso shape at the waist is produced, c) and auxiliary means extending in proximity to certain of said first control fabric panel portions to enhance the waist shape controlling functioning, d) said panel portions including a back panel at the garment rear to face the torso back at the waist, e) said back panel characterized as:

i) vertically elongated,
ii) horizontally unstretchable between horizontally spaced edges, there being generally vertically extending stays at said edges,
iii) said back panel having vertical dimension at least twice its maximum horizontal dimension between said edges.

2. The combination of claim 1 wherein said auxiliary means includes multiple elements which are yieldably resiliently stretchable in directions extending about said first control fabric panel portions.

3. The combination of claim 2 wherein said elements overlap vertically.

4. The combination of claim 2 wherein there are two sets of said elements, and an intermediate element which is substantially non-stretchable, in said directions.

5. In a torso-shape controlling, lower back supporting garment the combination comprising:
   a) said garment having first control fabric panel portions adapted to extend in waist shape controlling relation to torso front, back and sides,
   b) said control fabric panel portions including zones positioned to be generally rigid at the torso front and back and to yieldably resiliently stretch generally horizontally at the torso sides, whereby support is provided at the lower back, and an hourglass torso shape at the waist is produced,
   c) and auxiliary control fabric panel means wrapped about said first control fabric panel portions, and having end extents which are interconnected to cause said auxiliary panel means to exert inward compression against said first control fabric panel means,
   d) said garment first back panel portion having removable/adjustable overlap connection to an auxiliary back panel portion defined by said auxiliary control fabric panel means.

6. The combination of claim 5 wherein said auxiliary control fabric panel means includes multiple overlapping sub-panels which are yieldably resiliently stretchable in directions extending about said first control fabric panel portions.

7. The combination of claim 6 wherein said sub-panels overlap vertically.

8. The combination of claim 6 wherein there are two sets of said stretchable sub-panels, and an intermediate sub-panel which is substantially non-stretchable, in said directions.

9. The combination of claim 5 wherein said auxiliary control fabric panel means end extents have vertically adjustable removable connection to at least one of said first control fabric panel portions.

10. The combination of claim 5 wherein said first back panel portion and said auxiliary back panel portion have hook and pile interconnection, thereby to provide anti-twist mutual anchoring of said panel portions and the control fabric panel portions attached thereto.

11. In a torso-shape controlling, lower back supporting garment, the combination comprising:
    a) said garment having a series of upright fabric panels extending in waist shape controlling relation to torso front, back and sides, said panels including,
    b) a back panel at the garment rear to face the torso back at the waist,
    c) first and second control fabric panels and at the garment sides to face the wearer's torso at the waist opposite sides,
    d) first and second front panels at the garment front and that are adjustably interconnected to permit horizontal adjustment, and each characterized as horizontally unstretchable,
    e) third and fourth control fabric panels at the garment sides to face the wearer's torso at the waist opposite sides,
    f) and including a first adjustable tightening flap structure connected with said garment to extend about and overlie the control fabric panels, and to have tension transmitting adjustable connection to at least one of said front panels,
    g) said pack panel characterized as:
       i) vertically elongated,
       ii) horizontally unstretchable between horizontally spaced edges, there being generally vertically extending stays proximate said edges,
       iii) said back panel having vertical dimension at least twice its maximum horizontal dimension between said edges.

12. The combination of claim 10 including stays at said back panel and extending upright to transfer tensioning loading horizontally.

13. The combination of claim 10 wherein said stays are resiliently flexible and metallic.

14. The combination of claim 10 wherein said tightening flap structure includes tightening straps overlying said first, second, third, and fourth control panels, said straps having adjustable interconnection to permit controllable tightening of the garment about the torso waist.

15. The combination of claim 10 wherein said tightening flap structure has vertically adjustable connection to at least one of said front panels.

16. The combination of claim 11 including shoulder strap means attached to upper extents of certain of said control panels.

17. The combination of claim 16 wherein said shoulder strap means has adjustable vertical connection to the back panel.

18. The combination of claim 11 wherein said first and second control fabric panels are characterized in that:
    i) said first control panel is yieldably resiliently stretchable both horizontally and vertically between horizontally spaced edges, there being generally vertically extending stays at said respective edges of said first control panel,
    ii) said second control panel is generally resiliently stretchable, both horizontally and vertically, between horizontally spaced edges, there being generally vertically extending stays at said respective edges of said second control panel,
    iii) each of said first and second panels having vertical dimension exceeding its maximum horizontal dimension.

19. In a torso-shape controlling, lower back supporting garment, the combination comprising:
    a) said garment having a series of upright fabric panels extending in waist shape controlling relation to torso front, back and sides, said panels including,
    b) a back panel at the garment rear to face the torso back at the waist,
    c) first and second control fabric panels and at the garment sides to face the wearer's torso at the waist opposite sides,
    d) first and second front panels at the garment front and that are adjustably interconnected to permit horizontal adjustment, and each characterized as horizontally unstretchable, e) third and fourth control fabric panels at the garment sides to face the wearer's torso at the waist opposite sides, f) and including a first adjustable tightening flap structure connected with said garment to extend about and overlie the control fabric panels, and to have tension transmitting adjustable connection to at least one of said front panels, g) and wherein said third and fourth control fabric panels are characterized in that:
  i) said third control panel is yieldably stretchable both horizontally and vertically between horizontally spaced edges, there being generally vertically extending stays at said respective edges of the third control panel,
  ii) said fourth control panel is yieldably stretchable both horizontally and vertically between horizontally spaced edges, there being generally vertically extending stays at said respective edges of the fourth control panel,
  iii) each of said third and fourth control panels having vertical dimension exceeding its maximum horizontal dimension.

20. In combination:
 a) an inner garment wrapping about the torso and exerting pressure on the torso,
 b) an outer garment wrapping about the inner garment and exerting pressure on the torso via the inner garment,
 c) said garments having local mutually overlapping rear panels which are removably and adjustably interconnected by hook and pile means to provide rear adjustable mutual anchoring of said garment, and
 d) said garments having local mutually overlapping front panels which are removably and adjustably interconnected by hook and pile elements to provide front adjustable mutual anchoring of said garments.

21. The combination of claim 20 wherein each of said outer and inner garments has stretchable control panels between said front and back panels thereof.

* * * * *